(12) United States Patent
Sendai

(10) Patent No.: US 8,409,503 B2
(45) Date of Patent: Apr. 2, 2013

(54) COLORATION ANALYZING APPARATUS AND METHOD

(75) Inventor: Tomonari Sendai, Kanagawa-ken (JP)

(73) Assignee: Fujifilm Corporation, Tokyo (JP)

( * ) Notice: Subject to any disclaimer, the term of this patent is extended or adjusted under 35 U.S.C. 154(b) by 109 days.

(21) Appl. No.: 13/018,046

(22) Filed: Jan. 31, 2011

(65) Prior Publication Data

US 2011/0244591 A1 Oct. 6, 2011

(30) Foreign Application Priority Data

Mar. 31, 2010 (JP) ................................. 2010-080684

(51) Int. Cl.
*C12Q 1/68* (2006.01)
(52) U.S. Cl. ......... 422/50; 436/164; 436/523; 422/68.1; 422/408
(58) Field of Classification Search .................. None
See application file for complete search history.

(56) References Cited

U.S. PATENT DOCUMENTS

| | | | |
|---|---|---|---|
| 2003/0068638 A1 | 4/2003 | Cork et al. | |
| 2004/0146917 A1 | 7/2004 | Cork et al. | |
| 2007/0041624 A1 | 2/2007 | Cork et al. | |
| 2009/0093968 A1 | 4/2009 | Kawamata et al. | |
| 2009/0181470 A1 | 7/2009 | Chiku et al. | |
| 2011/0269247 A1 | 11/2011 | Chiku et al. | |

FOREIGN PATENT DOCUMENTS

| | | |
|---|---|---|
| JP | 2007-520701 A | 7/2007 |
| JP | 2009-216695 A | 9/2009 |
| WO | WO 2007/007849 A1 | 1/2007 |

OTHER PUBLICATIONS

Japanese Office Action dated Dec. 11, 2012 with a partial English translation.

*Primary Examiner* — Robert Xu
(74) *Attorney, Agent, or Firm* — McGinn IP Law Group, PLLC

(57) ABSTRACT

Viscosity of a test body solution spotted onto a test piece is detected. The test piece has an insoluble support, through which the test body solution is developed, and a test region formed on the insoluble support, the test region reacting with an analyte in the test body solution and undergoing coloration. A washing liquid is fed to the test region and its neighboring regions at the time between a stage, at which the test body solution has been developed through the test region, and a stage, at which a liquid for amplifying the coloration state of the test region is fed to the test piece, such that the quantity of the washing liquid fed to the test region and its neighboring regions is set to be large as the detected viscosity becomes high.

4 Claims, 5 Drawing Sheets

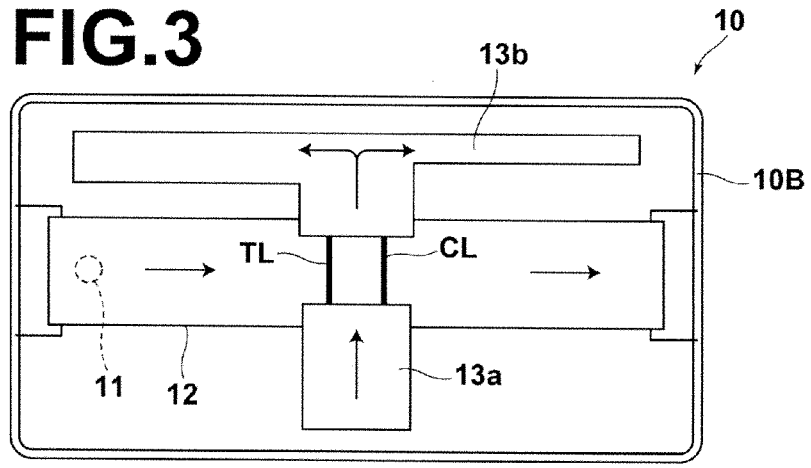
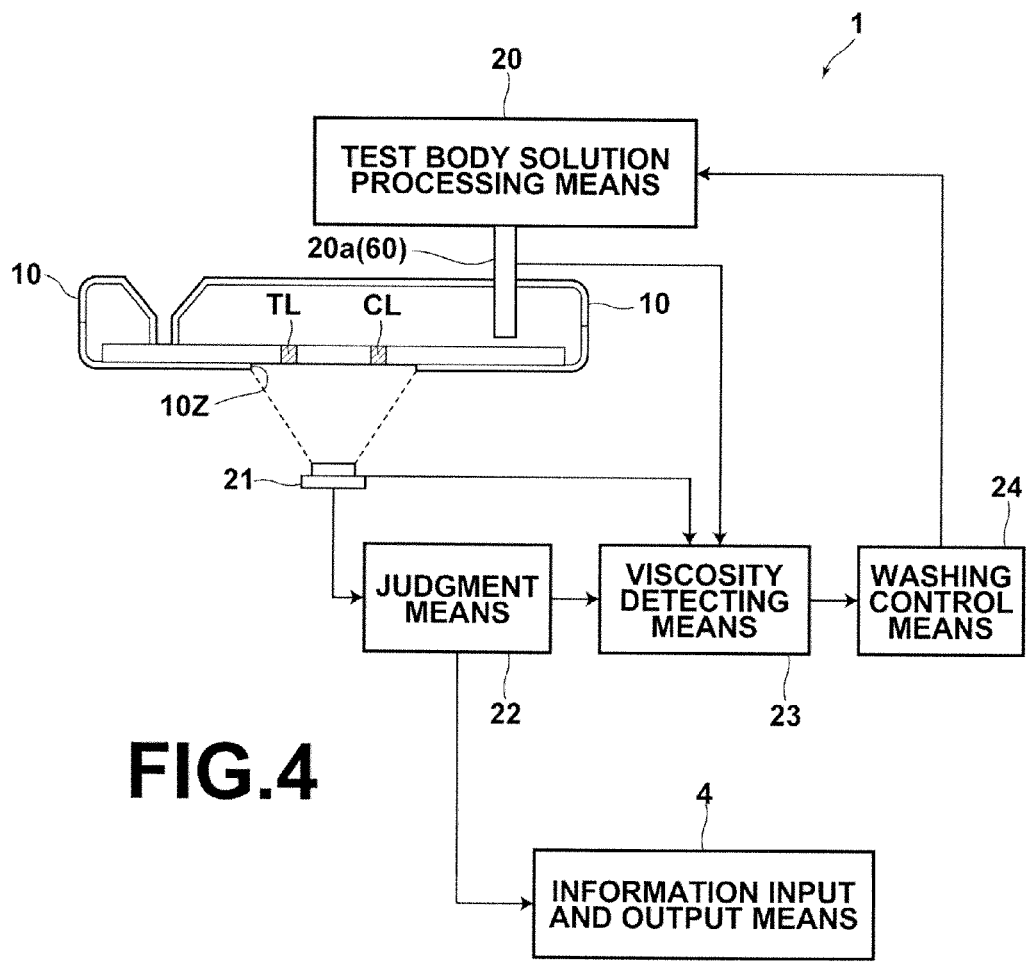

COLORATION ANALYZING APPARATUS AND METHOD

BACKGROUND OF THE INVENTION

1. Field of the Invention

This invention relates to a coloration analyzing apparatus and a coloration analyzing method for performing a quantitative analysis or a qualitative analysis of an analyte (i.e., a substance to be analyzed), which is contained in a test body solution.

2. Description of the Related Art

Recently, for examinations of external diagnostic medicines, poisons, and the like, there have been proposed various devices for feeding test body solutions, which have the possibility of containing analytes, to test pieces, and easily and quickly making examinations with respect to the analytes by use of immunochromatographic techniques. (Reference may be made to, for example, U.S. Patent Application Publication No. 20090093968.) For example, an insoluble support constituted of a porous material is prepared. The insoluble support is provided with a specific region (a test line), to which a first antibody that specifically binds with an analyte (e.g., an antigen) has been fixed. Also, a test body solution, which contains a mixture of a labeling second antibody that specifically binds with the analyte, and a test body having the possibility of containing the analyte, is developed through the insoluble support. As a result, an antigen-antibody reaction among the analyte, the first antibody, and the second antibody arises in the test line, and the test line is thus colored or develops color and comes into a coloration state. By observing the coloration state of the test line, it is quantitatively or qualitatively (negative/positive) analyzed whether the analyte is or is not present in the test body solution.

Also, in order for the coloration state of the test line to be detected quickly and with a high sensitivity, it has been proposed to perform amplification processing by use of an amplifying agent. (Reference may be made to, for example, U.S. Patent Application Publication No. 20090181470.) In U.S. Patent Application Publication No. 20090181470, it is disclosed that, with processing wherein, after the aforesaid test body solution has been developed through the insoluble support, and wherein an amplifying agent containing a metal ion, such as a silver ion, is developed through the insoluble support, the metal ion is bound with the complex of first antibody—analyte (antigen)—second antibody on the test line and thus amplifies the coloration state. It is also disclosed that a washing liquid is developed through the test region and its neighboring regions before the amplification processing is performed, and that noise due to the labeling substance, which is present at background regions, is thereby suppressed.

However, the test body solutions developed through the insoluble support have viscosities varying for different test body solutions. Some test body solutions may have a high viscosity, and other test body solutions may have a low viscosity. In cases where a predetermined quantity of the washing liquid is developed for performing the washing in the washing step, it often occurs that sufficient washing is not performed with respect to a test body solution having a high viscosity. If the amplification processing is performed in this state, the problems will occur in that washing non-uniformity and background noise arise, and in that the accuracy with which the analyte is analyzed becomes low.

SUMMARY OF THE INVENTION

The primary object of the present invention is to provide a coloration analyzing apparatus, wherein noise arising at the time of amplification processing due to a difference in viscosity of a test body solution is suppressed.

Another object of the present invention is to provide a coloration analyzing method, wherein noise arising at the time of amplification processing due to a difference in viscosity of a test body solution is suppressed.

The present invention provides a coloration analyzing apparatus for performing an analysis of a coloration state of a test piece provided with an insoluble support, through which a test body solution is developed, and a test region, which is formed on the insoluble support, the test region reacting with an analyte contained in the test body solution and undergoing coloration as a result of the reaction, the apparatus comprising:

i) viscosity detecting means for detecting viscosity of the test body solution, which has been spotted onto the test piece, ii) washing liquid feeding means for feeding a washing liquid, which is used for washing the test region and its neighboring regions, to the test piece at the time between a stage, at which the test body solution has been developed through the test region, and a stage, at which an amplifying liquid for amplifying the coloration state of the test region is fed to the test piece, and iii) washing control means for controlling the washing liquid feeding means such that the quantity of the washing liquid fed to the test piece is set to be large as the viscosity of the test body solution, which viscosity has been detected by the viscosity detecting means, becomes high.

The present invention also provides a coloration analyzing method for performing an analysis of a coloration state of a test piece provided with an insoluble support, through which a test body solution is developed, and a test region, which is formed on the insoluble support, the test region reacting with an analyte contained in the test body solution and undergoing coloration as a result of the reaction, the method comprising the steps of:

i) detecting viscosity of the test body solution, which has been spotted onto the test piece, and ii) feeding a washing liquid to the test region and its neighboring regions at the time between a stage, at which the test body solution has been developed through the test region, and a stage, at which an amplifying liquid for amplifying the coloration state of the test region is fed to the test piece, such that the quantity of the washing liquid fed to the test region and its neighboring regions is set to be large as the detected viscosity of the test body solution becomes high.

It is sufficient for the test region to come into the coloration state due to the presence of the analyte in the test body solution. For example, the test region may be of the type utilizing a chromatographic technique, particularly an immunochromatographic technique, in which immunoassay utilizing an antigen-antibody reaction is applied to the chromatographic technique. Also, each of the shape of the test region and the shape of a control region is not limited particularly. For example, each of the test region and the control region may be faulted in a line-like shape. Alternatively, each of the test region and the control region may have a predetermined pattern.

Also, the coloration state may be such that the test region forms color or discolors due to the presence of the analyte, or such that the control region forms color or discolors due to the test body solution. Further, the coloration state may be read out by readout means as image density values. The image density values may be the values representing the intensities of the formed color of the coloration state or the degrees of discoloring of the coloration state. Furthermore, the readout means may be selected from various constitutions, with which the coloration state of the test region is read out as the image density values. For example, the readout means may acquire an image of the test piece by use of an image pickup device. Alternatively, the readout means may be constituted such that light is irradiated to the test piece, and such that the light reflected from the test piece is received by a light receiving element. Also, the readout means may read out the changes in density of the coloration state as the image density values. Alternatively, the readout means may read out the intensities of the light (fluorescence) having a predetermined wavelength as the image density values.

The washing control means may employ one of various control techniques, with which the quantity of the washing liquid fed to the test piece is set to be large as the viscosity of the test body solution, which viscosity has been detected by the viscosity detecting means, becomes high. For example, the coloration analyzing apparatus in accordance with the present invention may be modified such that the washing control means controls the washing liquid feeding means such that the period of time, for which the washing liquid is fed from the washing liquid feeding means to the test piece, is set to be long as the viscosity of the test body solution, which viscosity has been detected by the viscosity detecting means, becomes high. Alternatively, the coloration analyzing apparatus in accordance with the present invention may be modified such that the washing control means controls the washing liquid feeding means such that the number of times of the feeding of the washing liquid from the washing liquid feeding means to the test piece is set to be large as the viscosity of the test body solution, which viscosity has been detected by the viscosity detecting means, becomes high.

Also, the coloration analyzing apparatus in accordance with the present invention should preferably be modified such that the washing control means previously stores the information representing a table, which represents the relationship between the viscosity of the test body solution and the washing liquid quantity, and the washing control means adjusts the quantity of the washing liquid, which is fed from the washing liquid feeding means to the test piece, in accordance with the table.

With the coloration analyzing apparatus and the coloration analyzing method in accordance with the present invention, the analysis is performed in the mariner described below with respect to the coloration state of the test piece provided with the insoluble support, through which the test body solution is developed, and the test region, which is formed on the insoluble support, the test region reacting with the analyte contained in the test body solution and undergoing the coloration as a result of the reaction. Specifically, the viscosity of the test body solution, which has been spotted onto the test piece, is detected. Also, the washing liquid is fed to the test region and its neighboring regions at the time between the stage, at which the test body solution has been developed through the test region, and the stage, at which the amplifying liquid for amplifying the coloration state of the test region is fed to the test piece. The feeding of the washing liquid is performed such that the quantity of the washing liquid fed to the test region and its neighboring regions is set to be large as the detected viscosity of the test body solution becomes high. Therefore, a noise source remaining in the test region and its neighboring regions is washed off certainly, and noise due to a residue, which has not been captured in the test region at the time of the amplification processing, is suppressed.

The coloration analyzing apparatus in accordance with the present invention may be modified such that the washing control means controls the washing liquid feeding means such that the period of time, for which the washing liquid is fed from the washing liquid feeding means to the test piece, is set to be long as the viscosity of the test body solution, which viscosity has been detected by the viscosity detecting means, becomes high. With the modification described above, the noise source remaining in the test region and its neighboring regions is washed off certainly in accordance with the level of the viscosity of the test body solution.

Alternatively, the coloration analyzing apparatus in accordance with the present invention may be modified such that the washing control means controls the washing liquid feeding means such that the number of times of the feeding of the washing liquid from the washing liquid feeding means to the test piece is set to be large as the viscosity of the test body solution, which viscosity has been detected by the viscosity detecting means, becomes high. With the modification described above, the noise source remaining in the test region and its neighboring regions is washed off certainly in accordance with the level of the viscosity of the test body solution.

BRIEF DESCRIPTION OF THE DRAWINGS

FIG. 3 is an explanatory sectional plan view showing the example of the test piece employed in the coloration analyzing apparatus in accordance with the present invention, FIG. 4 is a block diagram showing an embodiment of the coloration analyzing apparatus in accordance with the present invention.

DESCRIPTION OF THE PREFERRED EMBODIMENTS

The present invention will hereinbelow be described in further detail with reference to the accompanying drawings.

Figure 1:
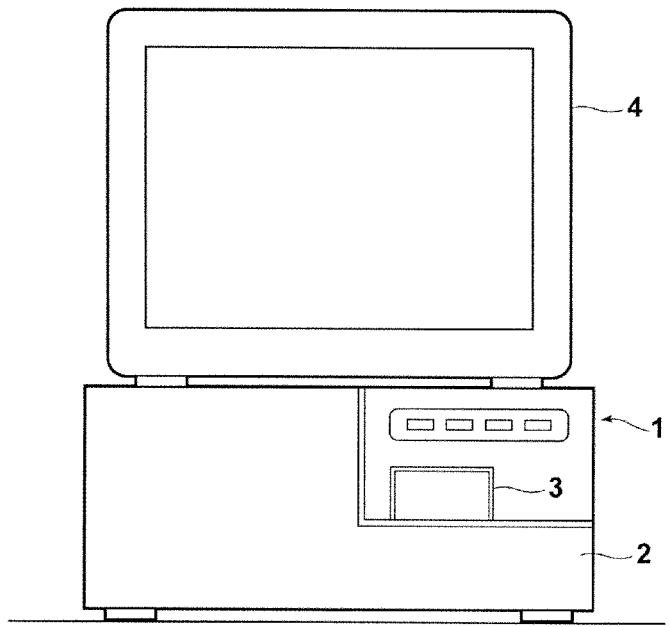
FIG. 1 is a schematic front view showing a constitution of an embodiment of the coloration analyzing apparatus in accordance with the present invention.

FIG. 1 is a schematic front view showing a constitution of an embodiment of the coloration analyzing apparatus in accordance with the present invention.

With reference to FIG. 1, a coloration analyzing apparatus 1, which is an embodiment of the coloration analyzing apparatus in accordance with the present invention, is constituted for performing readout of a coloration state from a test piece 10 for performing detection of an analyte by the utilization of, for example, the immunochromatographic technique. The coloration analyzing apparatus 1 comprises a case housing 2, a device insertion aperture 3, and information input and output means 4. The test piece 10, onto which a test body solution has been spotted, is inserted through the device insertion aperture 3. The coloration state arising as a result of a coloration reaction in the test piece 10 is read out optically. Also, information representing the result of the readout is outputted to the information input and output means 4. The information input and output means 4 is an operation panel constituted of, for example, a liquid crystal touch panel. The user inputs basic setting information for the analysis via the operation panel.

Figure 2:
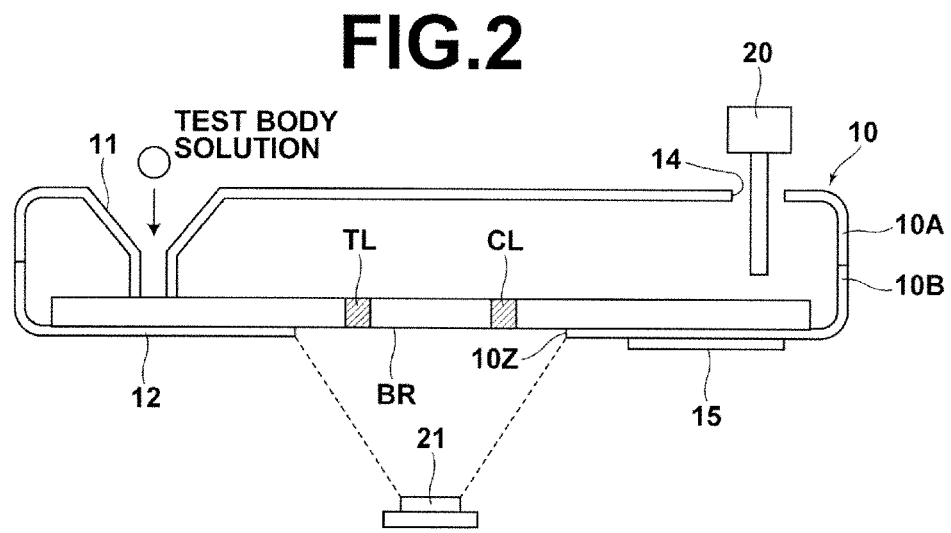
FIG. 2 is an explanatory sectional side view showing an example of a test piece employed in the coloration analyzing apparatus in accordance with the present invention.

FIG. 2 is an explanatory sectional side view showing an example of the test piece 10, from which the coloration state is read out by the coloration analyzing apparatus 1. FIG. 3 is an explanatory sectional plan view showing the example of the test piece 10, from which the coloration state is read out by the coloration analyzing apparatus 1. As the test piece 10, it is possible to employ one of known techniques as described in, for example, Japanese Unexamined Patent Publication Nos. 2009-139256 and 2007-064766.

As illustrated in FIG. 2, the test piece 10 is the device for performing a quantitative or qualitative (negative/positive) examination of an analyte by use of the immunochromatographic technique. In the test piece 10, the analyte (a predetermined antigen) is labeled such that the analyte becomes perceptible visually. A test body solution containing a mixture of a test body, which has the possibility of containing the analyte, and a labeling substance (a second antibody) is spotted onto the test piece 10.

The test piece 10 is provided with an upper casing 10A, a lower casing 10B, and an insoluble support 12. The insoluble support 12 is accommodated within the region surrounded by the upper casing 10A and the lower casing 10B. The upper casing 10A is provided with a through-hole 11, through which the test body solution is spotted from the exterior onto the insoluble support 12. The upper casing 10A is also provided with a through-hole 14, through which an amplifying liquid is spotted onto the insoluble support 12. The insoluble support 12 is secured to the inside bottom surface of the lower casing 10B. The lower casing 10B is provided with a viewing window 10Z for observation of the quantitative or qualitative analysis of the analyte. Also, an information storing means 15 is located on an outside bottom surface of the lower casing 10B. The information storing means 15 may be constituted of letter information, a bar code, an IC tag, or the like, for recording analyte identification information (the name of a patient, or the like), information representing the period of time required for the reaction, or the like.

The insoluble support 12 is constituted of an absorbing material, such as cellulose filter paper, glass fibers, or a polyurethane. The test body solution having been spotted onto the insoluble support 12 flows toward a predetermined direction by a capillary phenomenon through the insoluble support 12. The insoluble support 12 is provided with a test region (test line) TL and a control region (control line) CL. A first antibody, which has the specificity with respect to the analyte (the antigen), has been fixed to the test region TL in a line-like shape. In cases where the analyte is present in the test body, a binding product of first antibody—analyte—second antibody is formed in the test region TL, and the test region TL undergoes coloration in the line-like shape. A reference antigen (or antibody), which reacts with the labeling antibody, has been fixed to the control region CL. The reference antigen reacts with labeling antibody contained in the test body solution, and the control region CL undergoes coloration in a line-like shape. Therefore, by confirming the coloration state of the control region CL, a judgment is made as to whether the test body solution has or has not passed through the test region TL and the control region CL.

Further, as illustrated in FIG. 3, the test piece 10 is provided with a washing layer 13a and a washing layer 13b. The washing layer 13a and the washing layer 13b are located so as to sandwich the test region TL and the control region CL from the opposite sides of the test region TL and the control region CL (i.e., from the opposite sides taken with respect to the direction approximately perpendicularly intersecting with the flow path of the test body solution). The washing layer 13a and the washing layer 13b form a flow path of a washing liquid for washing the test region TL and the control region CL. The washing layer 13a and the washing layer 13b are constituted of the material identical with the material of the insoluble support 12. The washing liquid flows through the regions at which the washing layer 13a and the washing layer 13b are connected with the insoluble support 12. Therefore, in FIG. 3, the washing liquid flows through the test region TL, the control region CL, and their neighboring regions.

After the reaction in the test region TL and the reaction in the control region CL have been completed, the washing liquid is fed from test body solution processing means 20 shown in FIG. 2 to the test piece 10. As a result, the washing liquid flows by the capillary phenomenon from the washing layer 13a toward the side of the washing layer 13b. The washing liquid thus flows through the test region TL and the control region CL, which are located between the washing layer 13a and the washing layer 13b. In this manner, the labeling antibody, which did not take part in the formation of the immune complex in the test region TL and the immune complex in the control region CL, is removed.

Furthermore, as illustrated in FIG. 2, the upper casing 10A is provided with the through-hole 14 for developing the amplifying liquid, which contains the metal ion (such as silver colloid), from the test body solution processing means 20 to the insoluble support 12. After the test region TL and the control region CL have been washed by the washing liquid, the amplifying liquid is developed through the insoluble support 12. As a result, the metal ion is bound to the immune complex in the test region TL and the immune complex in the control region CL, and the coloration state of the test region TL and the coloration state of the control region CL are thus amplified by the metal ion.

FIG. 4 is a block diagram showing an embodiment of the coloration analyzing apparatus in accordance with the present invention. As illustrated in FIG. 4, the coloration analyzing apparatus 1 comprises the test body solution processing means (washing liquid feeding means) 20, readout means 21, judgment means 22, viscosity detecting means 23, and washing control means 24.

Figure 5:
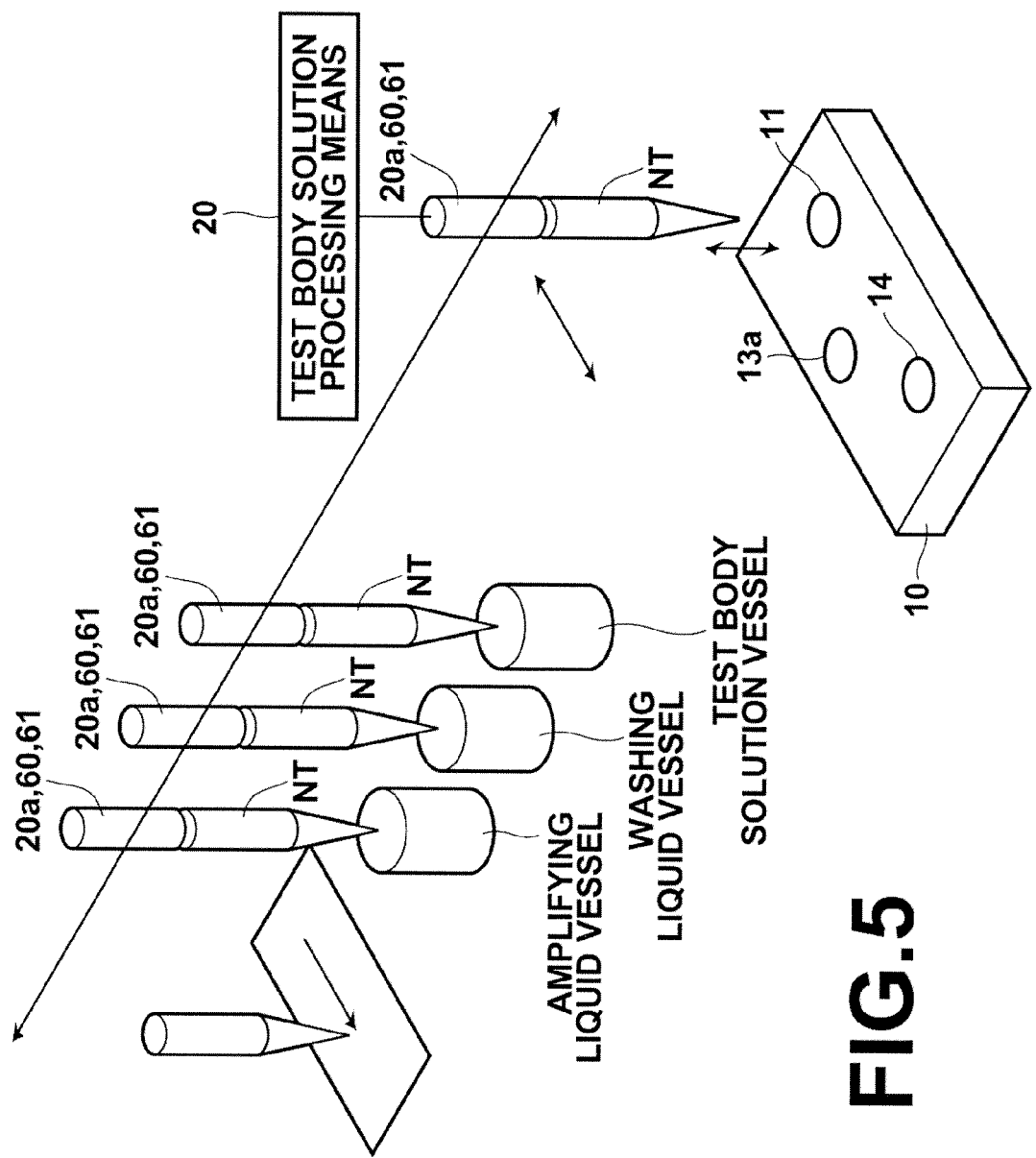
FIG. 5 is an explanatory perspective view showing an example of test body solution processing means shown in FIG. 4.

FIG. 5 is an explanatory perspective view showing an embodiment of the test body solution processing means 20 shown in FIG. 4. The example of the test body solution processing means 20 will be described hereinbelow with reference to FIG. 4 and FIG. 5. The test body solution processing means 20 feeds each of the liquids, which are necessary for the test body solution spotting step, the washing step, and the amplification step, to the test piece 10. The test body solution processing means 20 shown in FIG. 5 has the functions for automatically spotting each of the test body solution, the washing liquid, and the amplifying liquid onto the test piece 10. The test piece 10, a test body solution vessel which accommodates the test body solution, a washing liquid vessel which accommodates the washing liquid, the amplifying liquid vessel which accommodates the amplifying liquid, and a plurality of exchangeable nozzle tips (sampler tips) NT, NT, . . . for use at the time of the dispensing of the various kinds of the liquids are fitted previously to the coloration analyzing apparatus 1.

Also, at the time at which the beginning of the analysis has been instructed, the test body solution processing means 20 fits the nozzle tip NT to a nozzle holding section 20*a*, extracts the test body solution from the test body solution vessel, and dispenses the test body solution to the test piece 10. Thereafter, in the washing step, which is performed when a predetermined period of time has elapsed after the test body solution has been dispensed to the test piece 10, the test body solution processing means 20 extracts the washing liquid from the washing liquid vessel and dispenses the washing liquid to the test piece 10. Therefore, the test body solution processing means 20 acts as the washing liquid feeding means. Further, in the amplifying step, which is performed after the washing step has been finished, the test body solution processing means 20 extracts the amplifying liquid from the amplifying liquid vessel and dispenses the amplifying liquid to the test piece 10. At the time of the extraction of each of the liquids from the various kinds of the vessels, the test body solution processing means 20 sucks and discharges the liquid at a predetermined pressure for a predetermined period of time. As a result, a predetermined quantity of the liquid is extracted from the corresponding vessel and is dispenses to the test piece 10.

The readout means 21 shown in FIG. 4 reads out the coloration state of the test region TL and the coloration state of the control region CL as image density values through a viewing window 10Z. By way of example, the readout means 21 may be constituted of an image pickup device, such as a CCD or CMOS. The readout means 21 may read out the gray scale values as the image density values. Alternatively, the readout means 21 may read out R, G, and B component values as the image density values. As another alternative, the readout means 21 may read out the intensities of a predetermined color (a predetermined wavelength component) of the fluorescence, or the like, as the image density values. Further, the readout means 21 is not limited to the image pickup device and may be constituted of a light receiving device for receiving the reflected light or the fluorescence coming from the viewing window 10Z.

The judgment means 22 performs a qualitative or quantitative analysis in accordance with the image density values of the test region TL and the control region CL, which image density values have been read out by the readout means 21. Specifically, in accordance with the image density values of the control region CL, the judgment means 22 makes a judgment as to whether or not the test body solution has been developed normally through the insoluble support 12. Also, the judgment means 22 makes a judgment as to the quantity of the analyte or a positive/negative judgment in accordance with the image density values of the test region TL. Also, information representing the result of the judgment having been made by the judgment means 22 is outputted from the information input and output means 4.

The viscosity detecting means 23 detects the viscosity of the test body solution having been dispensed to the test piece 10. The viscosity detecting means 23 has the function for detecting the viscosity of the test body solution in accordance with a weight change $\Delta W$ of the test body solution having been dispensed to the test piece 10. Specifically, weight measuring means 60, which may be constituted of, for example, a strain gauge, is fitted to the nozzle holding section 20*a* shown in FIG. 5. The weight measuring means 60 has the function for measuring the weight change $\Delta W$ before the test body solution having been accommodated in the test body solution vessel is spotted onto the test piece 10 and after the test body solution has been spotted onto the test piece 10. As described above, at the time of the extraction of the test body solution from the test body solution vessel, the test body solution processing means 20 extracts and dispenses the test body solution at the predetermined pressure for the predetermined period of time. In such cases, if the viscosity of the test body solution varies, the weight of the test body solution, which is extracted and dispensed, will vary. On the basis of the characteristics described above, the viscosity detecting means 23 detects the viscosity of the test body solution in accordance with the weight change $\Delta W$.

Figure 6:
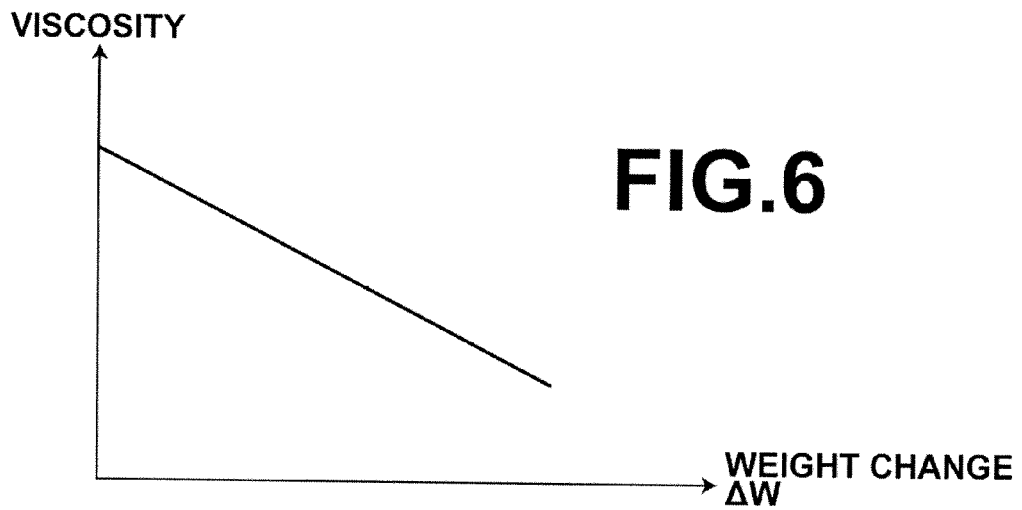
FIG. 6 is a graph showing an example of a table representing a relationship between a weight change of a test body solution having been dispensed to the test piece and viscosity of the test body solution, the information representing the table having been stored in viscosity detecting means shown in FIG. 4.

In this embodiment, the weight measuring means 60 is fitted to the nozzle holding section 20*a*. Alternatively, weight measuring means may be fitted to the site on which the test piece 10 is located, and the weight change $\Delta W$ of the test piece 10 may thus be measured. Also, FIG. 6 illustrates the example wherein the weight change $\Delta W$ and the viscosity have a relationship of a linear function. As for a certain kind of the test body and a certain kind of a reagent, it may occur that the weight change $\Delta W$ and the viscosity have a relationship of an exponential function or a power function. In such cases, the information representing the relationship of the exponential function or the power function may be stored in a storing table.

Further, as illustrated in FIG. 5, the coloration analyzing apparatus 1 may further comprise a temperature sensor 61 for detecting the temperature of the test body solution. The temperature sensor 61 is fitted to the nozzle holding section 20*a* of the test body solution processing means 20. At the time at which the test body solution is extracted from the test body solution vessel, the temperature of the test body solution is measured by the temperature sensor 61. By way of example, the viscosity detecting means 23 may store the information, which represents the relationship between the weight change $\Delta W$ and the viscosity with respect to each of different temperatures. (Reference may be made to FIG. 6.) Also, in accordance with the temperature and the weight change $\Delta W$, the viscosity detecting means 23 may make the judgment as to whether the viscosity falls or does not fall within a specified range. In such cases, in accordance with the findings that, in the cases of pure water, blood, and blood plasma, the viscosity, a kinematic viscosity, and a density of the liquid vary for different temperatures, the detection of the viscosity is performed accurately by use of the weight change $\Delta W$ and the temperature. Further, in the embodiment described above, the viscosity detecting means 23 detects the viscosity in accordance with the weight change $\Delta W$. Alternatively, the viscosity may be detected in accordance with the development rate of the test body solution.

Figure 7:
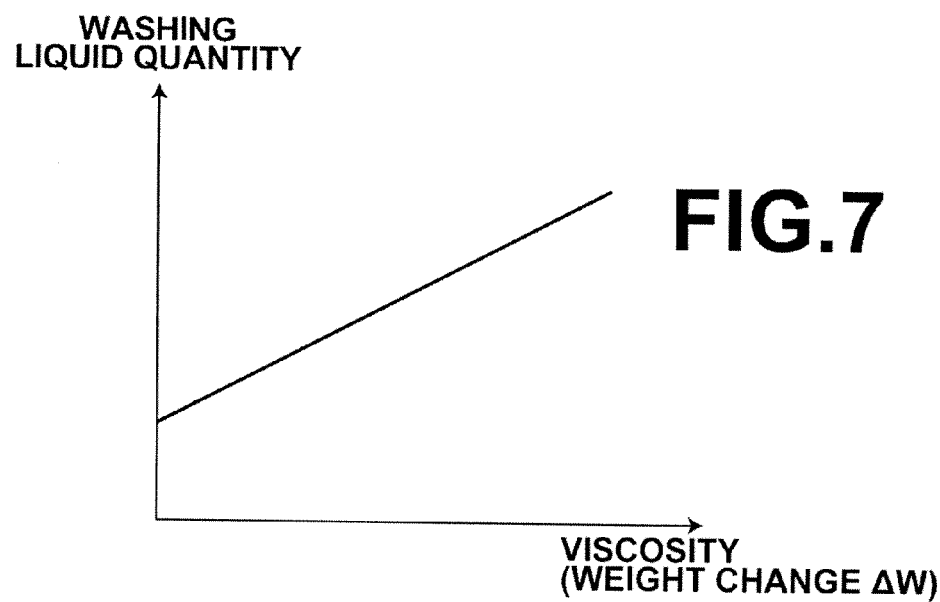
FIG. 7 is a graph showing how a quantity of a washing liquid is set to be large in accordance with the viscosity of the test body solution by washing control means shown in FIG. 4.

The washing control means 24 shown in FIG. 4 has the function for controlling the quantity of the washing liquid, which is used in the washing step, in accordance with the weight change $\Delta W$. Specifically, the washing control means 24 previously stores the information representing a table, which represents the relationship between the viscosity of the test body solution (the weight change $\Delta W$) and the washing liquid quantity as illustrated in FIG. 7. In accordance with the table, the washing control means 24 adjusts the quantity of the washing liquid, which is used in the washing step. Alternatively, in cases where the quantity of the washing liquid fed per unit time from the test body solution processing means 20 is fixed, the washing control means 24 may set the washing time to be long as illustrated in FIG. 8 and may thereby increase the total quantity of the washing liquid, which is fed to the test piece 10 in the washing step.

Figure 9:
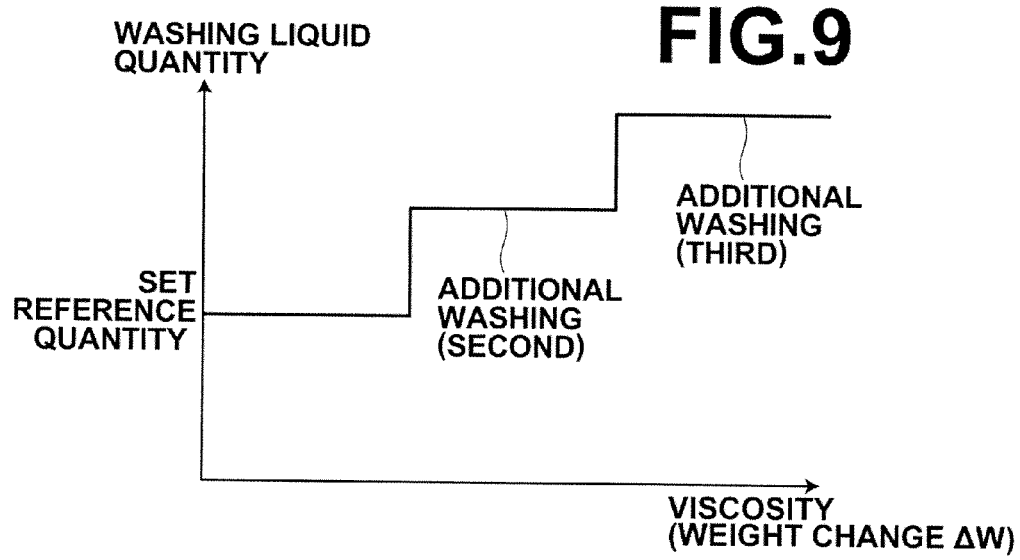
FIG. 9 is a graph showing how the number of times of washing is set to be large in accordance with the viscosity of the test body solution by washing control means shown in FIG. 4.

As another alternative, as illustrated in FIG. 9, the washing control means 24 may control the test body solution processing means 20 so as to perform additional washing in cases where the viscosity of the test body solution becomes higher than a set threshold value. In cases where the additional washing is performed, for example, the additional washing may be performed by use of a quantity of the washing liquid, which quantity is approximately half of the quantity of the washing liquid used in the ordinary washing step.

Figure 8:
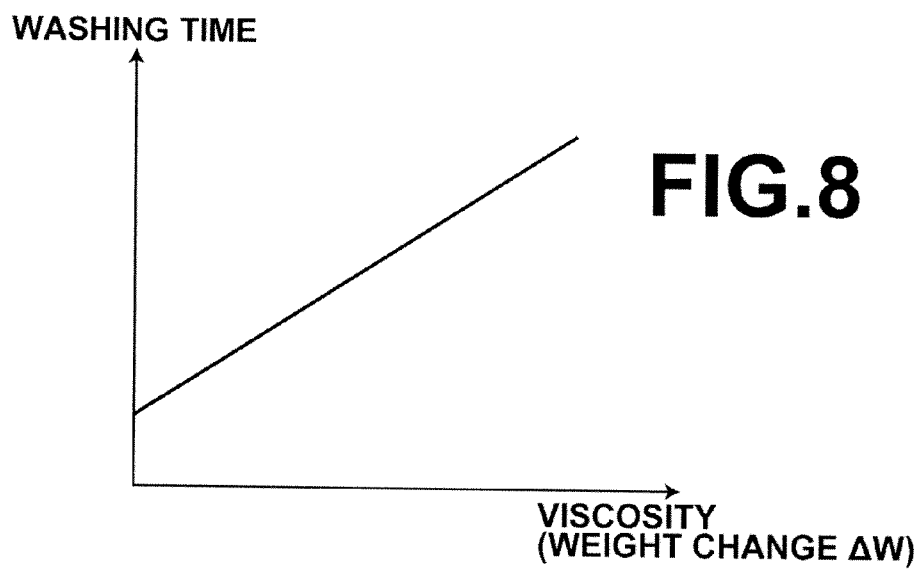
FIG. 8 is a graph showing how a washing time is set to be long in accordance with the viscosity of the test body solution by washing control means shown in FIG. 4.

Each of the tables illustrated in FIG. 7, FIG. 8, and FIG. 9 is obtained in the manner described below. Specifically, for example, test solutions varying in viscosity are prepared. After each of the test solutions has been developed through the insoluble support 12, washing is performed by setting the washing liquid quantity, the washing time, or the number of times of the washing at one of various different values. The result of the washing is confirmed by means of an image. Also, the washing liquid quantity, or the like, associated with the state, in which the image density change due to non-uniformity, and the like, on the image becomes lower than a predetermined value, is evaluated previously. The relationship between the viscosity of the test body solution and the washing liquid quantity, or the like, is thus obtained. FIG. 7 illustrates the example wherein the viscosity of the test body solution and the washing liquid quantity have a proportional relationship. Also, FIG. 8 illustrates the example wherein the viscosity of the test body solution and the washing time have a proportional relationship. As for a certain kind of the test body and a certain kind of a reagent, it may occur that the viscosity of the test body solution and the washing liquid quantity or the washing time have a relationship of an exponential function or a power function. In such cases, the information representing the relationship of the exponential function or the power function may be stored in a storing table.

As described above, the quantity of the washing liquid fed to the test piece 10 is controlled in accordance with the viscosity of the test body solution. Therefore, even in cases where the viscosity of the test body solution is high, the test body solution remaining in the test region TL and background regions BR other than the control region CL is washed off certainly, and the amplification of the remaining test body solution by the amplification processing is thereby prevented.

Figure 10:
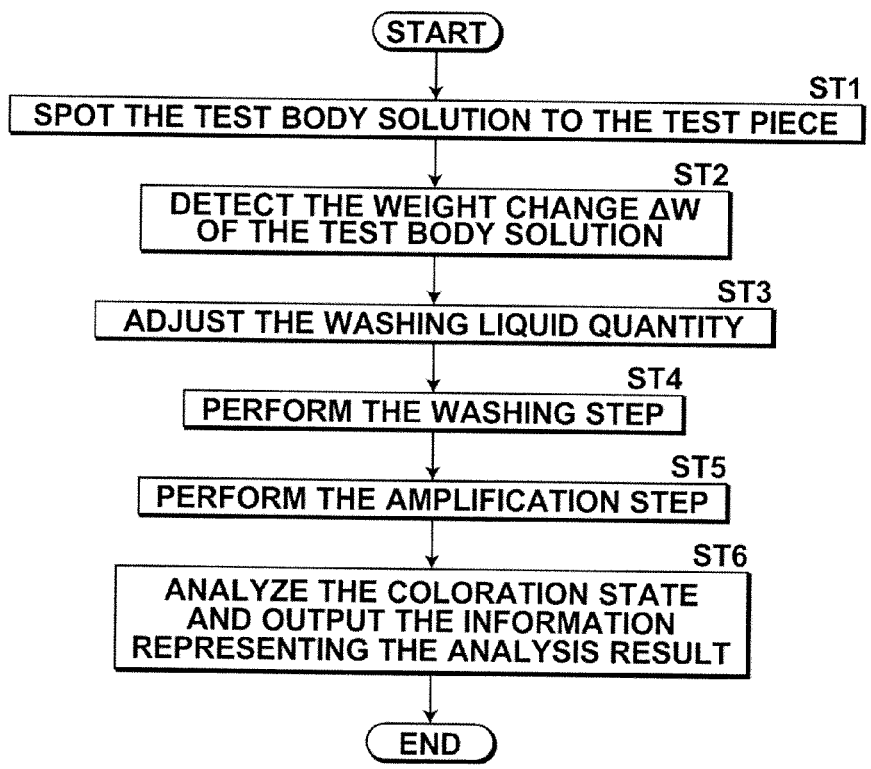
FIG. 10 is a flow chart showing an embodiment of the coloration analyzing method in accordance with the present invention.

FIG. 10 is a flow chart showing an embodiment of the coloration analyzing method in accordance with the present invention. The embodiment of the coloration analyzing method in accordance with the present invention will be described hereinbelow with reference to FIG. 1 through FIG. 10. Firstly, in a step ST1, as illustrated in FIG. 5, the test piece 10, the test body solution vessel, and the like, are loaded to the coloration analyzing apparatus 1, and the test body solution is spotted onto the test piece 10 by the test body solution processing means 20. At this time, in a step ST2, the weight measuring means 60 measures the weight change ΔW before the test body solution is dispensed to the test piece 10 and after the test body solution has been dispensed to the test piece 10. Also, the viscosity detecting means 23 detects the viscosity of the test body solution in accordance with the weight change ΔW. Also, in a step ST3, as illustrated in FIG. 7, FIG. 8, or FIG. 9, the quantity of the washing liquid is adjusted by the washing control means 24 in accordance with the viscosity of the test body solution.

In a step ST4, when a predetermined period of time has elapsed after the test body solution has been spotted onto the test piece 10, the washing liquid is dispensed from the test body solution processing means 20 to the test piece 10. At this time, as illustrated in FIG. 3, the washing of the test region TL and the control region CL is performed in accordance with the quantity of the washing liquid adjusted by the washing control means 24. Also, in a step ST5, as illustrated in FIG. 5, when the washing step has been finished, the amplifying liquid is dispensed to the test piece 10 by the test body solution processing means 20. Thereafter, in a step ST6, the coloration state of the test region TL having been subjected to the amplification processing is read out as the image density values, and the quantitative analysis or the qualitative analysis of the analyte is made in accordance with the image density values of the test region TL by the judgment means 22.

With the embodiment described above, the analysis is performed in the manner described below with respect to the coloration state of the test piece 10 provided with the insoluble support 12, through which the test body solution is developed, and the test region TL, which is formed on the insoluble support 12, the test region TL reacting with the analyte contained in the test body solution and undergoing the coloration as a result of the reaction. Specifically, the viscosity of the test body solution, which has been spotted onto the test piece 10, is detected. Also, the washing liquid is fed to the test region TL and its neighboring regions at the time between the stage, at which the test body solution has been developed through the test region TL, and the stage, at which the amplifying liquid for amplifying the coloration state of the test region TL is fed to the test piece 10. The feeding of the washing liquid is performed such that the quantity of the washing liquid fed to the test region TL and its neighboring regions is set to be large as the detected viscosity of the test body solution becomes high. Therefore, a noise source remaining in the test region TL and its neighboring regions is washed off certainly, and noise due to a residue, which has not been captured in the test region TL at the time of the amplification processing, is suppressed.

The embodiment may be modified such that, as illustrated in FIG. 8, the washing control means 24 controls test body solution processing means (the washing liquid feeding means) 20 such that the period of time, for which the washing liquid is fed from the test body solution processing means 20 to the test piece 10, is set to be long as the viscosity of the test body solution, which viscosity has been detected by the viscosity detecting means 23, becomes high. With the modification described above, the noise source remaining in the test region TL and its neighboring regions is washed off certainly in accordance with the level of the viscosity of the test body solution.

Alternatively, the embodiment may be modified such that, as shown in FIG. 9, the washing control means 24 controls the test body solution processing means (the washing liquid feeding means) 20 such that the number of times of the feeding of the washing liquid from the test body solution processing means 20 to the test piece 10 is set to be large as the viscosity of the test body solution, which viscosity has been detected by the viscosity detecting means 23, becomes high. With the modification described above, the noise source remaining in the test region TL and its neighboring regions is washed off certainly in accordance with the level of the viscosity of the test body solution.

The coloration analyzing apparatus in accordance with the present invention is not limited to the embodiment described above and may be embodied in various other ways. For example, in the embodiment described above, the test piece 10 has the single judgment line (the single test region TL). Alternatively, the test piece may have at least two test regions TL, TL. Also, in the embodiment described above, the test body solution processing means 20 automatically spot the test body solution onto the test piece 10. Alternatively, the test body solution may be previously spotted onto the test piece 10, and the test piece 10 may then be loaded to the coloration analyzing apparatus 1. In such cases, the readout means 21 may detect the rate of the development of the test body solution through the insoluble support 12, and the viscosity detecting means 23 may detect the viscosity of the test body solution in accordance with the development rate of the test body solution.

Further, in the embodiment described above, the quantity of the washing liquid is altered in cases where the viscosity of the test body solution is outside the specified range. Alternatively, in order for the flow rate of the test body solution to be controlled, a pressure or a suction pressure at the time of the spotting of the test body solution may be altered, and the temperature of the test body solution may be controlled.

Furthermore, in the embodiment described above, the detection of the viscosity of the test body solution is performed in accordance with the weight change $\Delta W$. Alternatively, for example, the insoluble support illustrated in FIG. 2 and FIG. 3 may be monitored by use of an image sensor (the readout means 21), the period of time elapsing between the stage, at which the spotting of the test body solution is begun, and the stage, at which the test body solution reaches a predetermined position in the insoluble support 12, may be measured, and the viscosity of the test body solution may thus be detected.

What is claimed is:

1. A coloration analyzing apparatus for performing an analysis of a coloration state of a test piece provided with an insoluble support, through which a test body solution is developed, and a test region, which is formed on the insoluble support, the test region reacting with an analyte contained in the test body solution and undergoing coloration as a result of the reaction, the apparatus comprising:
    i) viscosity detecting means for detecting viscosity of the test body solution, which has been spotted onto the test piece,
    ii) washing liquid feeding means for feeding a washing liquid, which is used for washing the test region and its neighboring regions, to the test piece at the time between a stage, at which the test body solution has been developed through the test region, and a stage, at which an amplifying liquid for amplifying the coloration state of the test region is fed to the test piece, and
    iii) washing control means for controlling the washing liquid feeding means such that the quantity of the washing liquid fed to the test piece is set to be large as the viscosity of the test body solution, which viscosity has been detected by the viscosity detecting means, becomes high.

2. A coloration analyzing apparatus as defined in claim 1 wherein the washing control means controls the washing liquid feeding means such that the period of time, for which the washing liquid is fed from the washing liquid feeding means to the test piece, is set to be long as the viscosity of the test body solution, which viscosity has been detected by the viscosity detecting means, becomes high.

3. A coloration analyzing apparatus as defined in claim 1 wherein the washing control means controls the washing liquid feeding means such that the number of times of the feeding of the washing liquid from the washing liquid feeding means to the test piece is set to be large as the viscosity of the test body solution, which viscosity has been detected by the viscosity detecting means, becomes high.

4. A coloration analyzing apparatus as defined in claim 1 wherein the washing control means previously stores the information representing a table, which represents the relationship between the viscosity of the test body solution and the washing liquid quantity, and
    the washing control means adjusts the quantity of the washing liquid, which is fed from the washing liquid feeding means to the test piece, in accordance with the table.

* * * * *